US010751074B2

(12) United States Patent
Baur et al.

(10) Patent No.: US 10,751,074 B2
(45) Date of Patent: Aug. 25, 2020

(54) METHOD OF MANUFACTURING A SURGICAL INSTRUMENT WITH INCREASED RELIABILITY

(71) Applicant: ERBE ELEKTROMEDIZIN GMBH, Tuebingen (DE)

(72) Inventors: Thomas Baur, Rottenburg (DE); Juergen Hiller, Dettingen (DE); Viktoria Rydzewski, Nuertingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 526 days.

(21) Appl. No.: 15/482,335

(22) Filed: Apr. 7, 2017

(65) Prior Publication Data
US 2017/0273701 A1 Sep. 28, 2017

Related U.S. Application Data

(63) Continuation of application No. 13/648,380, filed on Oct. 10, 2012, now abandoned.

(30) Foreign Application Priority Data

Oct. 12, 2011 (EP) .................................... 11184918

(51) Int. Cl.
B29C 45/14 (2006.01)
A61B 17/29 (2006.01)
A61B 18/14 (2006.01)
(52) U.S. Cl.
CPC .......... A61B 17/29 (2013.01); A61B 18/1445 (2013.01); B29C 45/14 (2013.01); A61B 2017/2948 (2013.01)

(58) Field of Classification Search
None
See application file for complete search history.

(56) References Cited

U.S. PATENT DOCUMENTS

| 4,842,540 A | * | 6/1989 | Endo ................... B29C 45/1615 264/267 |
| 5,059,378 A | | 10/1991 | Petterson et al. |
| 5,766,167 A | | 6/1998 | Eggers et al. |
| 5,810,876 A | | 9/1998 | Kelleher |
| 5,855,590 A | | 1/1999 | Malecki et al. |
| 5,958,317 A | * | 9/1999 | Aguadisch ............. A01N 25/34 264/159 |
| 5,984,939 A | | 11/1999 | Yoon |
| 2009/0017147 A1 | | 1/2009 | Lintner et al. |
| 2010/0234687 A1 | | 9/2010 | Azarbarzin et al. |

(Continued)

FOREIGN PATENT DOCUMENTS

DE 89 10 462 U1 1/1990
DE 298 04 860 U1 7/1999
(Continued)

Primary Examiner — Edmund H Lee
(74) Attorney, Agent, or Firm — Blank Rome LLP

(57) ABSTRACT

A surgical instrument having a long shaft comprises, in the shaft, a sealing element produced by primary shaping at the installation location. The sealing element is produced such that any actuating mechanisms are installed and held in place in the shaft and then a curable plastic material is injected into the shaft such that the material encloses the actuating element along a length that is greater than the inside diameter and smaller than its length.

7 Claims, 4 Drawing Sheets

(56) References Cited

U.S. PATENT DOCUMENTS

| | | | | |
|---|---|---|---|---|
| 2011/0266714 A1* | 11/2011 | Lewis | ................... | B21K 1/16 |
| | | | | 264/267 |
| 2012/0289773 A1 | 11/2012 | Joshi et al. | | |
| 2016/0176089 A1* | 6/2016 | Kast | ................... | B60J 10/24 |
| | | | | 264/267 |

FOREIGN PATENT DOCUMENTS

| | | |
|---|---|---|
| DE | 10 2010 040 667 | 3/2011 |
| GB | 2217355 | 10/1989 |
| JP | H10272139 A | 10/1998 |
| WO | WO-97/41783 | 11/1997 |
| WO | WO-2004/091377 | 10/2004 |
| WO | WO-2008/091377 | 7/2008 |
| WO | WO-2010/009525 | 1/2010 |

\* cited by examiner

METHOD OF MANUFACTURING A SURGICAL INSTRUMENT WITH INCREASED RELIABILITY

CROSS-REFERENCE TO RELATED APPLICATIONS

This application is a continuation of U.S. patent application Ser. No. 13/648,380, filed on Oct. 10, 2012, now abandoned, which claims priority to European patent application EP 11 184 918.8, filed on Oct. 12, 2011, the entire disclosures of which are incorporated by reference herein.

TECHNICAL FIELD

Embodiments of the invention relate to a surgical instrument, particularly to a single-use or multiple-use endoscopic instrument.

BACKGROUND

Surgical instruments are used, for example, for clamping and closing, as well as, optionally, for severing clamped and closed blood vessels. Such instruments have been disclosed in, for example, DE 298 04 860 U1, U.S. Pat. No. 5,984,939, US 2010/0234687, WO 2010/009525 A1, DE 10 2010 040 667 A1, WO 2004/091377 A2, WO 97/41783, US 2009/017147 A1, WO 2008/020964 A2 and U.S. Pat. No. 5,855,590. The disclosed instruments, most of them being provided for laparoscopic or endoscopic use, commonly comprise an elongated shaft that extends away from a grip. Attached to the distal end of the shaft is a tool that can be moved, via an actuating device, with the use of the grip. A transmission mechanism establishes a driving connection between the actuating device and the tool. The transmission mechanism is e.g., a pull wire that extends through the tubular shaft. Naturally, a certain play must exist between the pull wire and the inside wall of the shaft to ensure ease of movement of the pull wire.

Surgical instruments are used in a moist environment. If moisture such as, for example, tissue fluid of any type, rinsing fluid or the like, enters a surgical instrument, this can result in electrical or other malfunctions. This is at least true for single-use surgical instruments. In multiple-use surgical instruments, it is also possible for fluid to enter the housing during the sterilization processes needed between different uses, which can cause failures in the housing.

SUMMARY

In view of the above, it is an object of the embodiments disclosed herein to provide an improved surgical instrument.

The instrument in accordance with the present disclosure may be a single-use instrument (i.e., a one-time use) or it may also be an instrument that can be sterilized and suitable for multiple uses. The disclosed instrument has an elongated shaft comprising, on one end, a tool that has, for example, a movable part and comprising, on another end, a grip with an actuating device for the tool. At least one transmission mechanism extends through the elongated shaft, said transmission mechanism transmitting a movement of the actuating device to the tool. A sealing body is arranged in the shaft; said sealing body can be a separately fabricated sealing element that is inserted in the shaft or it can also be produced in said shaft by primary shaping.

In conjunction with this disclosure, separate fabrication or separately fabricated is understood to mean any manufacture within or outside the operations of the manufacturer of the instrument. These sealing elements may be those that are commercially available or those that are specifically manufactured.

Primary shaping is understood to mean any production of the sealing element from an initially shapeless paste material. This paste material is introduced in a flowable state, for example, in a pulpy or viscous state or a plastically viscous state, into the shaft and closes the passage that exists in said shaft. Desirably, in doing so, the transmission mechanism(s) is (are) already arranged in the shaft. After the shapeless material has penetrated, said material becomes the sealing element because the shapeless material assumes a solid, optionally elastic, state. This can be accomplished by chemical and/or physical processes. For example, the formation of the sealing element can be accomplished by cooling a paste that has been liquefied e.g., by the application of heat, curing, chemical reactions, cross-linking, drying or other processes. Chemical cross-linking can be triggered and effected by chemical accelerators. Rapidly binding two-component mixtures are used, these mixtures being prepared just before or during insertion. Physical cross-linking triggers may include e.g., radiation (e.g., UV-radiation), to trigger or effect curing. The material that is selected for the sealing element may be any material exhibiting self-lubricating properties.

The sealing element that is installed in the shaft or formed in the shaft blocks the passage of fluid, vapor, gases, aerosols, dust, smoke and the like. In doing so, the at least one transmission mechanism extends through the sealing element. Desirably, the transmission mechanism is arranged in the sealing element so it is movable in longitudinal direction. This can be accomplished by various measures. For example, the actuating mechanism may have a relatively smooth, metallic surface.

Once the sealing element, e.g., by injection of a shapeless mass, has hardened and the actuating mechanism is moved for the first time in a longitudinal direction, the shearing forces acting between the sealing element and the actuating mechanism overcome the adhesive forces existing between the actuating mechanism and the sealing element. The potentially existing bond between the transmission mechanism and the sealing element is separated at least in part (desirably fully). The sealing element and the transmission mechanism remain in frictional abutment. Inasmuch as the contact surface between the sealing element and the actuating mechanism is clearly smaller than the contact surface between the sealing element and the inner wall of the shaft, it is ensured that during a first actuation the sealing element remains in place and the outer bond with the shaft is not separated. The gap forming between the actuating mechanism and the sealing element has a gap width of zero. This is enough to prevent the penetration of moisture, gasses or other particles. Fluid or solid particles potentially seated on the movable transmission mechanism are stripped from the surface of the actuating mechanism by the sealing element. Thus, there is no tracking them into the housing by pump effects or the like.

Within the framework of the present disclosure, it is possible to take additional or other measures to produce the sealing element by primary shaping, with said sealing element abutting in a tight and gap-free manner against the actuating mechanism. For example, the actuating mechanism may have an anti-adhesive coating such as, for example, a PE coating, PTFE coating, silicone oil layer or the like. Non-shrinking materials such as, for example, silicone rubber of the alkoxy silicone type, are particularly suitable. Desirably, water-repellent (hydrophobic) substances are used for making the sealing element. These substances effectively prevent the entering of fluid in a gap, whatever shape it may be, between the sealing element and the actuating mechanism. The aforementioned stripping effect is reliably provided. The introduction of moisture into the interior of the grip part due to the longitudinal movement of the actuating mechanism is effectively prevented.

The sealing element may be compact (without pores). As needed, it may also have a certain pore volume, in which case a closed-cell structure is desired. However, open-cell structures can also be used. For example, the sealing element consists of an open-cell foamed material. Such a material also prevents the passage of fluids, at least for a certain time; particularly when the foam has a water-repellent finish. It is also possible to use other materials such as e.g., felt, in particular felt containing swellable fibers. These concepts are particularly suitable for use in single-use devices.

The transmission mechanism is desirably a wire or a thin rod of metal or plastic material. The transmission mechanism is at least suitable for the transmission of pull forces. It may also be designed for the transmission of push forces. If the transmission mechanism is made of metal or of any other electrically conductive material, it may transmit mechanical movements as well as electrical energy. If the transmission mechanism is a wire or a thin rod of plastic material, it is desired to select a plastic material that will not combine with the material of the sealing element, e.g., silicone, or that will only adhere minimally (or not at all) to said sealing element.

If the transmission mechanism is made of metal, it is desirably polished. This means that the metal surface is smooth and free of an additional coating such as, for example, insulation. However, insulation or an anti-adhesive layer may be applied to the polished wire, covering the entire length or a part of said wire, if desired. The insulation may extend to parts that are not in contact with the sealing element and/or also to parts that extend through the sealing element.

The instrument may comprise a tool with one or more movable parts. A movably arranged part may perform a linear motion such as, for example, in a longitudinal shaft direction, or also an axial motion about a center of motion. The movable parts may be associated with one or more transmission mechanisms that extend through the shaft and the sealing element. Desirably, the transmission mechanisms are independent of each other and can thus perform relative movements with respect to each other. The sections of the transmission mechanisms extending through the sealing element are desirably straight and oriented in the direction of movement. In doing so, an unimpaired movement of the transmission mechanisms sliding through the sealing element is ensured.

Desirably, the sealing element consists of a non-shrinking material. Thus, it can be ensured that said sealing element closes the entire cross-section of the shaft and guarantees good tightness. As mentioned above, the sealing element may be made of a hydrophobic material. The actuating mechanism may also comprise hydrophobic material, for example, plastic material, or the actuating mechanism may be coated with hydrophobic material (especially to the section of the actuating mechanism that extends through the sealing element). Such a coating can prevent the penetration of water into the interior of the housing even when certain pressure differences exist as may occur, for example, when a surgical instrument is being sterilized. Likewise, considerable pressure differences may occur in the use of single-use devices, for example, during insufflation.

Desirably, the sealing element has a length that is clearly shorter than the length of the shaft, whereby said length is desirably greater than the diameter of the shaft. As such, tightness is guaranteed on the one hand and the ease of movement of the at least one transmission mechanism is maintained on the other hand. When sealing materials defining a low frictional value with the employed transmission mechanism are used and, for example, themselves display self-lubricating properties, the sealing element may also take up more than half the length of the shaft, e.g., its entire length.

In principle, it is possible to arrange the sealing element so as to be movable in the shaft. In such an embodiment, the transmission mechanism may be connected with the sealing element in a material-bonded and/or frictional and/or form-fitted manner. Desirably, however, the sealing element is held in the shaft in a material-bonded and/or frictionally engaged and/or form-fitting matter. This ensures that, even after extended use, the sealing element will not migrate but stay in place, whereas the actuating mechanism may slide back and forth through the sealing element.

BRIEF DESCRIPTION OF THE DRAWINGS

Hereinafter, exemplary embodiments of the invention are explained in greater detail with reference to drawings, in which.

DETAILED DESCRIPTION

Figure 1:
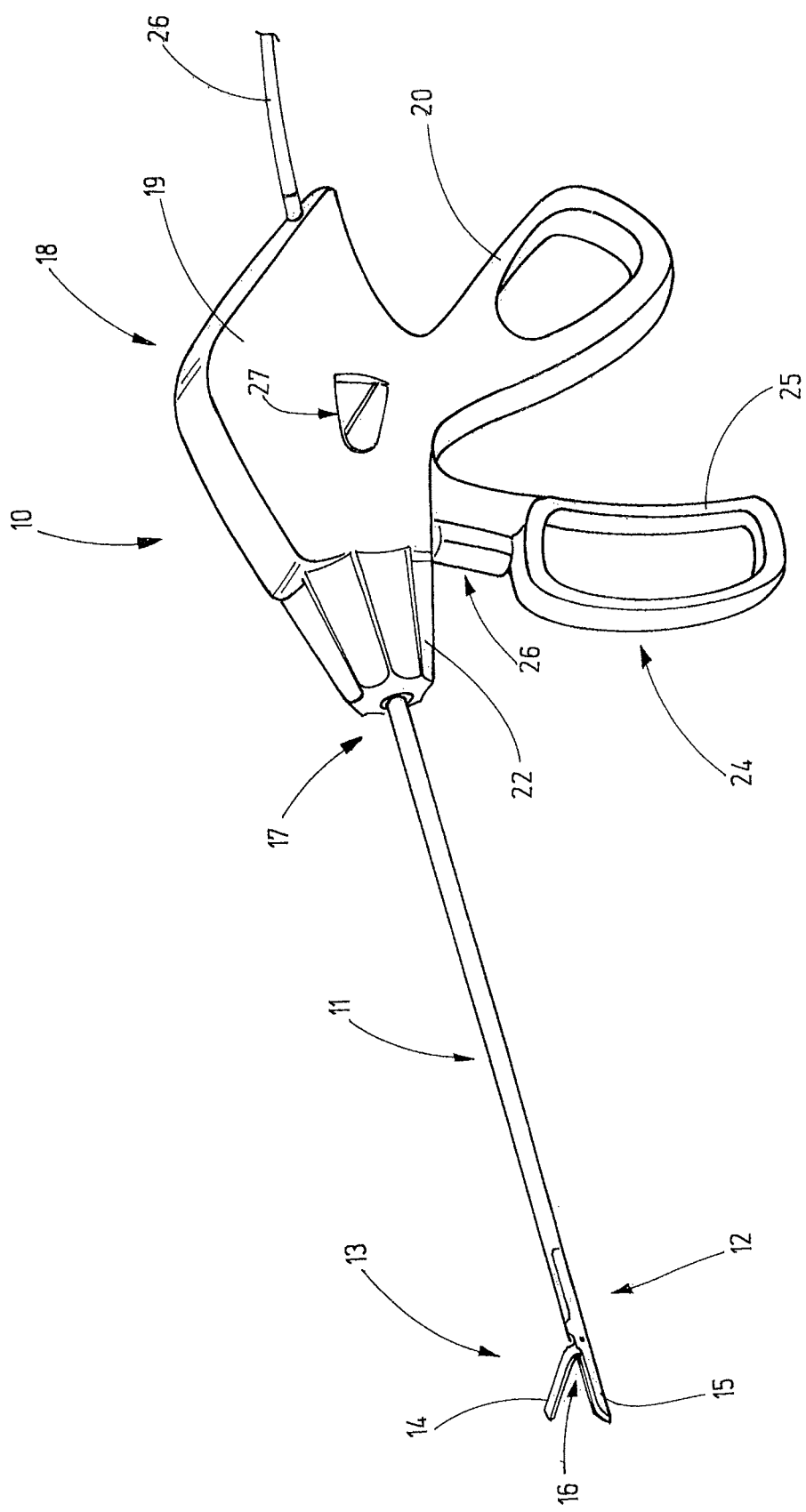
FIG. 1 is a perspective general view of the instrument in accordance with the disclosed principles.

FIG. 1 shows a surgical instrument 10 that can be used, for example, in endoscopic or laparoscopic operations and also in open surgery. The instrument 10 shown in FIG. 1 is only an example of the types of instruments to which the disclosed embodiments can be applied. The instrument 10 is used for clamping and closing blood vessels. If necessary, it can also be designed for severing a closed blood vessel.

Figure 2:
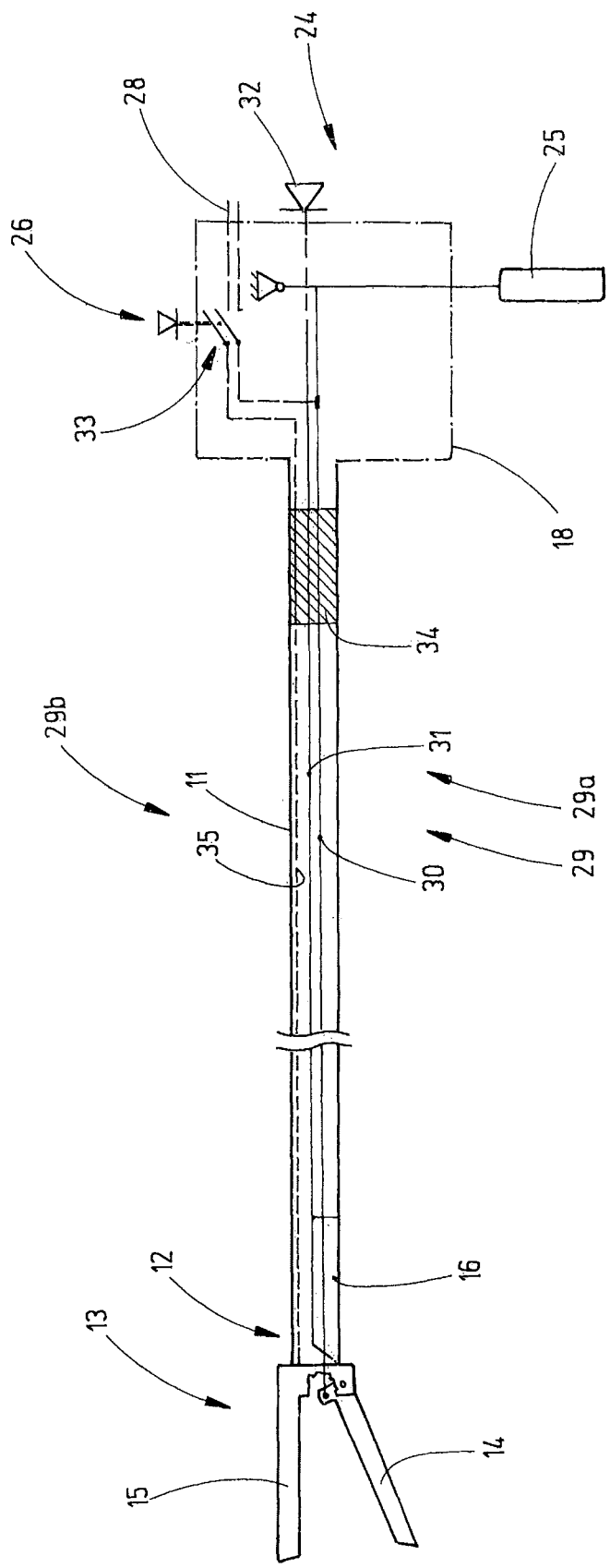
FIG. 2 is a schematic representation of the FIG. 1 instrument.

The instrument 10 has a longitudinal, desirably straight, shaft 11 that, desirably, may have a diameter of, e.g., only a few millimeters and a length of a few decimeters. To this extent, it should be appreciated that FIG. 1 is not true to scale. On its distal end 12, the shaft 11 holds a tool 13 that is made to interact with biological tissue such as e.g., a vessel. The tool 13 comprises at least one movable part 14 that can be supported, e.g., to be movable in a pivoting motion relative to another part 15. If necessary, it is also possible for both parts 14, 15 to be movable in a pivoting motion. In addition, this tool 13 may also comprise a knife 16 that is better seen in FIG. 2 and, e.g., is supported to be movable in a longitudinal direction. The knife 16 that normally is in a retracted position as schematically indicated in FIG. 2, can be used, e.g., for severing a closed vessel held between the parts 14, 15, said vessel having been closed by coagulation, for example, in that said knife is pushed forward in a longitudinal direction. To accomplish this, the parts 14, 15 can be provided with appropriate recesses or slits.

Furthermore, the shaft 11 has a proximal end 17 that is held on a grip 18. The grip 18 may be configured as a housing and may comprise an upper housing part 19 and a lower grip part 20. The housing part 19 and/or the grip part 20 are desirably hollow.

Figure 3:
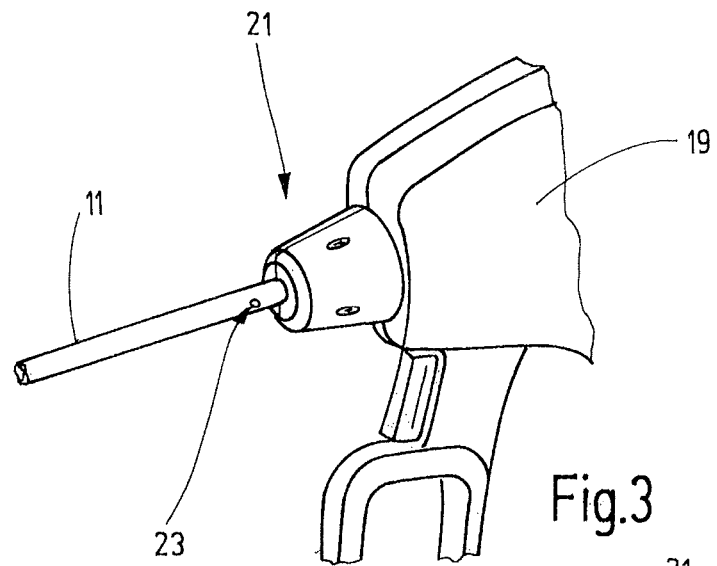
FIG. 3 illustrates the instrument of FIG. 1, with the cap removed.
Figure 4:
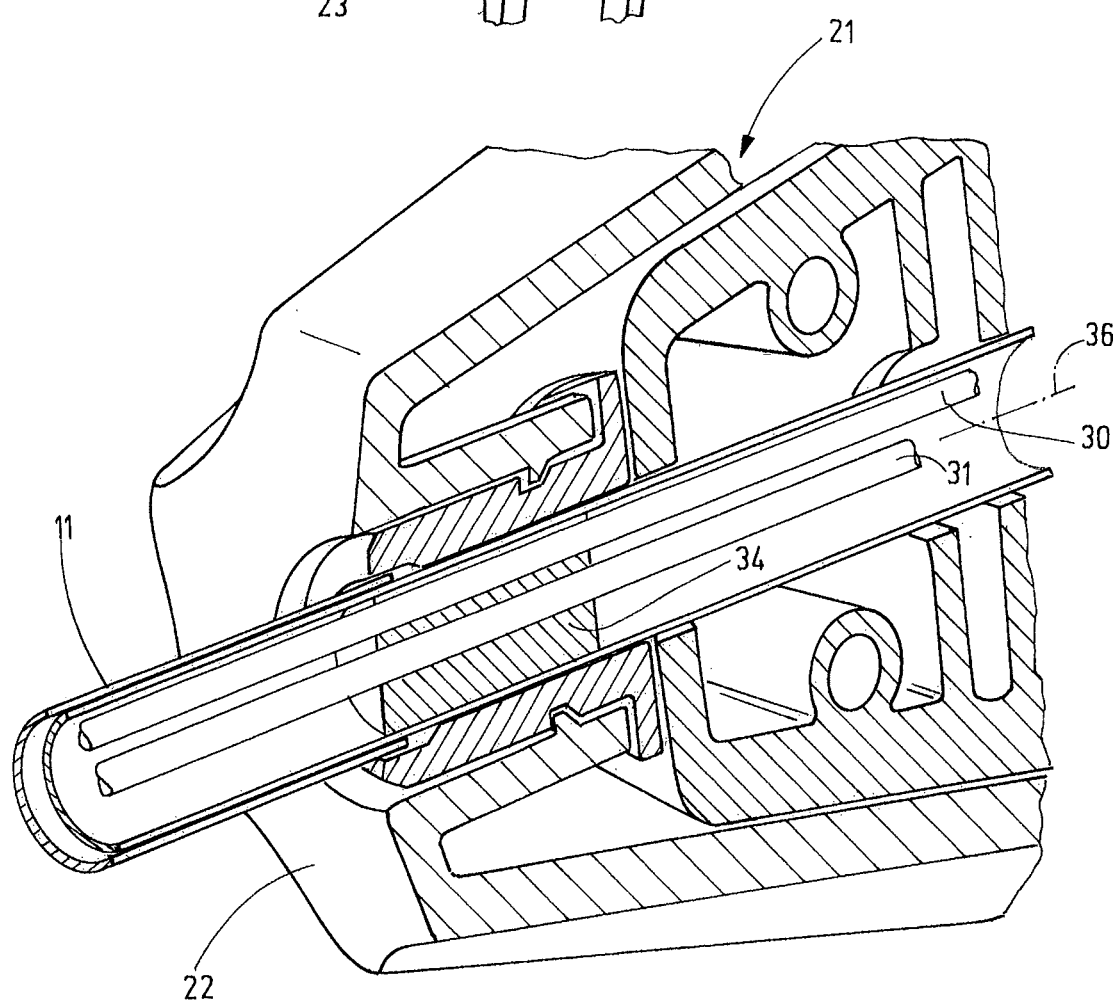
FIG. 4 is a perspective illustration of a section of the FIG. 1 instrument, sectioned in the region of a sealing element.

A coupling or connecting device 21, as is shown in FIGS. 3 and 4, is used for connecting the proximal end 17 of the shaft 11 to the housing part 19. On its end facing the shaft 11, the housing part 19 has a conical attachment over which normally extends a rotary chuck 22. During use, the rotary chuck 22 is disposed to rotate the shaft 11 into a desired rotary position about the longitudinal axis of said shaft 11. To accomplish this, the rotary chuck 22 may be in engagement with an appropriate hole 23 provided in the proximal end 17 of the shaft 11.

An actuating device 24 for the tool may be provided on the grip 18, particularly on the housing part 19. This actuating device 24 may e.g., comprise a pivotally supported hand lever 25 that can be pivoted toward the grip part 20 or away from said grip part 20. In addition, the actuating device 24 may comprise additional actuating mechanisms such as e.g., a trigger 26 and/or an additional actuating lever 27. In addition, a line 28 extends away from the housing 18; the line 28 may be configured as an electrical cable. The cable leads to e.g., a power-supplying medical device that supplies the tool 13 with electrical power when needed.

As shown in FIG. 2, the tool 13 is connected with the actuating device 24. To do so, the at least one transmission mechanism 29 longitudinally extends through the hollow shaft 11. The transmission mechanism 29 may be e.g., a wire consisting of plastic material or metal, said wire predominantly acting as e.g., a pulling mechanism. One end of said wire may be connected to part 14 of the tool 13, and the other end of said wire may be connected to the hand lever 25, either directly or via a transmission mechanism.

Additional transmission mechanisms 29a, 29b may extend through the hollow shaft 11, e.g., in the form of a slightly thicker wire or a rod 31 that can transmit push forces. One end of the rod 31 may be connected to the knife 16. Another end of the rod 31 may be connected to a separate actuating mechanism 32 or also to a locking and coupling device that is controlled e.g., by the actuating device 24. For example, it is possible to connect the knife 16 to the hand lever 25 using the locking and coupling device to be actuated by said hand lever. The locking and coupling device can be controlled by the lever 27.

The trigger 26 may be disposed to connect part 15 of the tool 13 to one pole of a voltage source, desirably an RF voltage source. The wire 30 may act as an electrical conductor and connect part 14 to the other pole of the electrical power source when needed. The single-pole or double-pole wire switch 33 actuated by the trigger 26 can establish or interrupt the connection between the line 28 and the parts 14, 15 of the tool 13.

Arranged in the shaft 11 is a sealing element 34 that blocks the passage that extends through the shaft 11 in a longitudinal direction and through which extends the transmission mechanisms 29, 29a, 29b (i.e., specifically, wire 30, rod 31 and, optionally, the electrical line 35 indicated in dashed lines in FIG. 2). Line 35 is a non-moving element that e.g., simply connects the switch 33 to part 15 of the tool 13. Line 35, for example, is an insulated wire. In contrast, transmission mechanism 29 or 29a, i.e., wire 30 or rod 31, for example, are respectively arranged to be longitudinally movable. They extend parallel to the shaft middle line 36 and are moved back and forth in this direction. Consequently, they are movably arranged in the sealing element 34.

Figure 5:
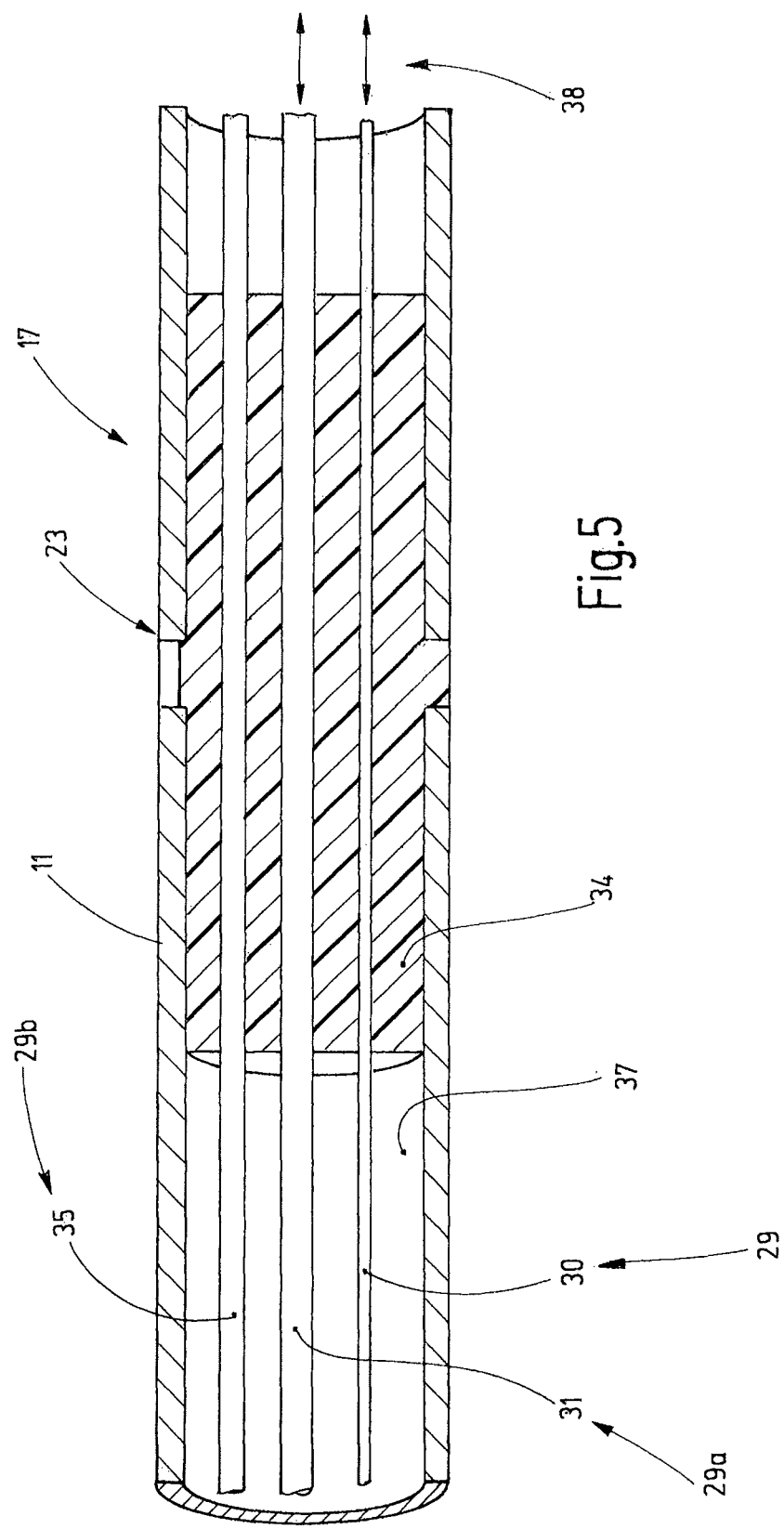
FIG. 5 is an illustration of the shaft, the actuating mechanism extending through said shaft and of the sealing element, in a longitudinal cross-sectional view.

Reference is now made to FIG. 5, which shows a section of the shaft 11 that is near the grip 18 (i.e., the proximal end 17). In an exemplary embodiment, this part of the shaft 11 contains the sealing element 34, through which the transmission mechanisms 29, 29a, 29b (e.g., wire 30, rod 31 and line 35) extend. The arrangement of the sealing element 34 at the proximal end of the shaft 11 minimizes the tendency of transmission mechanism 29 to kink when said shaft is pushed in the direction toward the tool 13. However, it may also be advantageous and, optionally, be desirable to arrange the sealing element 34 at another point, e.g., on the distal end 12, or at a point between the distal end 12 and the proximal end 17 of the shaft 11.

Desirably, the sealing element 34 consists of an elastic plastic material displaying little or no shrinkage such as e.g., a cross-linked silicone. In particular, the plastic materials selected from the multitude of available silicone materials are those that display little shrinkage or swelling and are water-repellent, in particular. The sealing element 34 may have a poreless, compact body. However, other materials may also be selected. For example, the sealing element may have a pore volume and be a closed-cell foam to offer increased elasticity. Other materials such as open-celled foams or felts may also be used. If needed, they may also be swellable in water to swell and form a seal against the entry of water.

The sealing element 34 can be manufactured separately and be installed as an element in the shaft 11 during the assembly of the instrument 10. In doing so, said element 34 is secured on the interior wall of the shaft 11, e.g., in a form-fitting, frictionally engaged or material-bonded manner. The transmission mechanisms 29, 29a, 29b extending through the sealing element 34 desirably extend, without a gap or at least substantially without a gap, through the sealing element 34 so that they can be smoothly moved back and forth in a longitudinal direction 36.

In another embodiment, the sealing element 34 is produced by primary shaping at the installation location. To accomplish this, the transmission mechanism(s) 29 is (are) first arranged in the shaft 11 and, thereafter, the still not-cured sealing element 34 material is injected through a suitable opening, e.g., the hole 23, into the interior of the shaft 11. The still not-cured material fills the passage and encloses the transmission mechanism(s) 29. In doing so, a material-bonded adhesion is established between the sealing element 34 and the interior wall 37 of the shaft 11. Furthermore, when curing, the sealing element 34 may come into form-fitted engagement with one or more structures of the shaft 11. For example, one or more projections of the sealing element 34 may extend into one or more holes 23 and cure therein. A form-fitting toothing may faun between the sealing element 34 in the shaft 11 so that the sealing element 34 is secured in a longitudinal position in the shaft 11, said sealing element having been formed in said longitudinal position. For curing of the material of the sealing element 34, it is possible—depending on the type of material that is used—to employ any one suitable measure that has been mentioned hereinabove.

The above explained principles may be employed to arrange and/or faun one or more sealing elements 34 in the shaft 11. Each of the sealing elements may be arranged on the distal end 12, proximal end 17, or in between the ends.

The sealing elements 34 may be arranged at a distance from each other or without a distance between each other.

At the latest, when the transmission mechanisms 29 are moved for the first time in the direction of arrows 38, a potential superficial adhesion between the transmission mechanism 29 and the sealing element 34 is eliminated due to the resultant concentration of shearing forces. Starting at this point, the sealing element 34 forms an effective barrier due to the gap-free abutment against the surface of the transmission mechanisms 29 (e.g., wire 30 and/or rod 31), said barrier acting not only against aqueous fluids, but also against vapors, gases, dust, smoke or the like. Thus, the sealing element 34 effectively seals the passage otherwise extending from the tool 13 into the interior of the housing of the grip 18.

A surgical instrument 10 having a long shaft 11 comprises, in the shaft 11, a sealing element 34 that has been produced by primary shaping at the installation location. Desirably, the sealing element 34 is produced such that, first, any one or more actuating mechanisms 29 are installed and held in place in the shaft 11, and then a curable plastic material that is disposed to form the sealing element 34 is injected into the shaft 11 such that the material encloses the actuating element 30, 31 along a length that is desirably greater than the inside diameter and smaller than its length. Desirably, the curable material is injected along a length of one or a few centimeters in the shaft that has, e.g., a length of several decimeters and, desirably, a diameter of at most a few millimeters.

What is claimed is:

1. A method of manufacturing a surgical instrument, the method comprising:
   providing a longitudinal shaft having a proximal end and a distal end;
   providing at least one tool on the distal end;
   providing a grip on the proximal end;
   providing at least one actuating device on the grip;
   providing at least one transmission mechanism through the shaft, the at least one transmission mechanism being movable in said shaft to transmit a movement of the actuating device to the tool; and
   forming, by primary shaping, a sealing element in the longitudinal shaft to form a seal around the at least one transmission mechanism by injecting through an opening in the shaft an unsolidified sealing material to enclose the at least one transmission mechanism in the shaft and solidifying the sealing material.

2. The method of claim 1, wherein the solidifying comprises curing the sealing material to form the sealing element.

3. The method of claim 1, wherein the opening is a hole in a wall of the longitudinal shaft.

4. The method of claim 1, wherein the injecting results in the sealing material filling less than all of the longitudinal shaft.

5. The method of claim 2, wherein the curing step results in a material-bonded adhesion between the sealing element and an interior wall of the longitudinal shaft.

6. The method of claim 2, wherein the curing step results in a form-fitting toothing between the sealing element and the longitudinal shaft.

7. The method of claim 1, wherein the sealing element is formed such that the sealing element is not in contact with the proximal end of the shaft.

\* \* \* \* \*